July 29, 1958 F. W. ANDERSON Plant Pat. 1,738
PEACH TREE
Filed Dec. 27, 1957
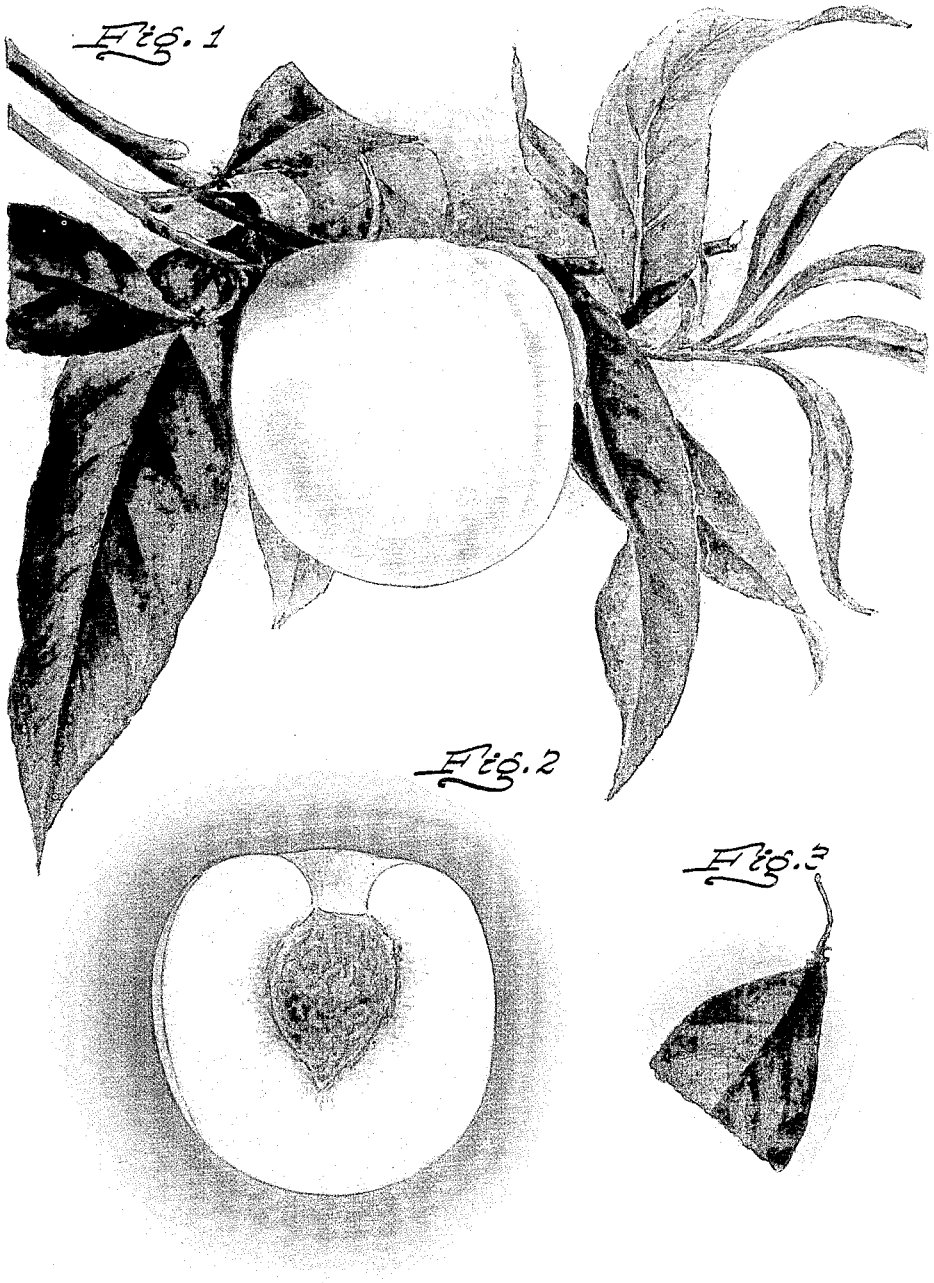
WITNESS
Addison E Avery
INVENTOR:
Frederic W. Anderson
Webster & Webster
ATTYS.

United States Patent Office

Plant Pat. 1,738
Patented July 29, 1958

1,738

PEACH TREE

Frederic W. Anderson, Merced, Calif., assignor to Kim Bros., Reedley, Calif., a partnership doing business under the fictitious name of Reedley Nursery Application December 27, 1957, Serial No. 705,728

1 Claim. (Cl. 47—62)

This invention relates to a new and distinct variety of peach tree which bears large, firm, yellow-fleshed freestone fruit of excellent quality for commercialization as a market and dessert peach.

The variety was originated by me in my fruit breeding orchard, located near Merced, California, during a continuing program in the development of commercially desirable fruit varieties.

The herein claimed variety is a cross between the Le Grand nectarine (United States Plant Patent No. 549) and the Royal Hale peach (United States Plant Patent No. 1,247).

More particularly, flowers of a Le Grand nectarine tree were fertilized with pollen from a Royal Hale peach tree, and of the seedlings grown from the resulting seeds approximately one-half were nectarines, while the remaining one-half were peaches.

When such seedling peach trees—which were under continuing observation by me—came into bearing, one thereof, and which is the instant variety, was very promising, and I therefore selected it for subsequent reproduction.

Asexual reproduction of the instant variety of peach tree was accomplished by me, in my orchard located as aforesaid, by top-working on mature orchard trees, and such reproductions were found to run true in all respects.

An important characteristic of the present variety of peach tree is that it bears fruit of generally the same type but which ripens approximately one week later than the Royal Hale and J. H. Hale peaches, and thus desirably extends the marketing season for such type of peach; the J. H. Hale peach being unpatented.

In comparison to the Rio Oso Gem peach (United States Plant Patent No. 84) the ripening period of the fruit is at about the same time, and there is general similarity in size, color, and firmness of the flesh. However, the fruit of the present variety is distinctive in that it is more nearly round, with a smooth instead of a rough suture line, is much less acid in taste, and of better eating quality. Additionally, the tree is larger, more vigorous, and quite productive in comparison to said Rio Oso Gem peach tree.

In the drawings:

Fig. 1 is an elevation showing one of the fruits, together with a twig and leaves.

Fig. 2 is a sectional elevation of one of the fruits, with the stone exposed.

Fig. 3 is a fragmentary elevation of one of the leaves.

Referring now more specifically to the pomological details of this new and distince variety of peach tree, the following is an outline description thereof; all major color plate identifications being by reference to Maerz and Paul Dictionary of Color, except where common terms of color definition are employed:

Tree:
- *Size.*—Large.
- *Vigor.*—Vigorous.
- *Growth.*—Spreading.

- *Production.*—Productive.
- *Bearing.*—Regular bearer.

Trunk: Size—stocky.

Branches:
- *Size.*—Medium.
- *Texture.*—Medium.
- *Lenticels.*—Number—medium. Size—medium.

Leaves:
- *Size.*—Large. Average length, 6½". Average width, 1⅜".
- *Color.*—Top side—medium green (22–L–7). Under side—lighter green (21–L–7).
- *Margin.*—Glandular; crenate.
- *Petiole.*—Medium length; medium thickness.
- *Glands.*—Average number—four. Opposite; medium size; reniform; usually positioned two on petiole and two to four on blade.

Flowers:
- *Blooming period.*—Mid season, usually a day or two before the Elberta peach (unpatented).
- *Size.*—Large.
- *Fertility.*—Self-fertile, with red anthers before anthesis.

Fruit: Date of first picking—August 8, 1957. Date of last picking—August 18, 1957.
- *Maturity when described.*—Eating ripe—August 15, 1957.
- *Size.*—Uniform; large. Average diameter axially, 3" to 4". Average transversely in suture plane, 3" to 4".
- *Form.*—Uniform; symmetrical; globose to slightly oblong.
- *Suture.*—An inconspicuous line; shallow; slight depression beyond pistil point.
- *Ventral surface.*—Rounded slightly; lips equal.
- *Cavity.*—Rounded. Average depth, ½". Average breadth, 1½". Markings—smooth.
- *Base.*—Rounded.
- *Apex.*—Short.

Skin:
- *Thickness.*—Medium.
- *Texture.*—Medium.
- *Tendency to crack.*—None.
- *Down.*—Moderate.
- *Color.*—Yellow (9–K–6, shading to 10–L–8), partially overspread with orange red (3–J–12), shading to a deeper red or maroon (7–L–6).

Flesh:
- *Amygdalin.*—Moderate.
- *Juice.*—Abundant to moderate.
- *Texture.*—Firm; meaty; melting.
- *Fibers.*—Fine.
- *Ripens.*—Even.
- *Flavor.*—Delicate; lacks the acidity of the Rio Oso Gem.
- *Aroma.*—Distince.
- *Eating quality.*—Good to best.
- *Color.*—Yellow (9–K–8) near skin, shading intermediate to a lighter yellow (9–J–5), with a whitish yellow (9–B–2) near the stone; the flesh immediately adjacent the stone or cavity being streaked with purple red (6–A–6).

Stone:
- *Type.*—Freestone.
- *Fibers.*—Short; parts from flesh smoothly.
- *Size.*—Medium. Average length, 1½". Average breadth, 1⅜". Average thickness, ¾".
- *Form.*—Oval.
- *Base.*—Straight.
- *Hilum.*—Broad.
- *Apex.*—Acute.
- *Sides.*—Equal.

*Surface.*—Irregularly furrowed near base; pitted throughout.
*Ridges.*—Jagged; continuous.
*Pits.*—Elongated.
*Ventral edge.*—Thick, without wing toward base.
*Dorsal edge.*—Full, with deep broad groove.
*Tendency to split.*—Slight.
*Color.*—Brown (7–A–12 to 8–L–6), shading toward purple (7–A–5) at base.

Use: Market; dessert.
Keeping quality: Good.
Shipping quality: Good.

The tree and its fruit herein described may vary in slight detail due to climatic and soil conditions under which the variety may be grown.

The following is claimed:

A new and distinct variety of peach tree, as illustrated and described, which bears large, firm, yellow-fleshed, freestone fruit having a yellow surface color partially blushed with red, and particularly characterized by ripening approximately one week later than the Royal Hale and J. H. Hale peaches and about with the Rio Oso Gem peach; further characterized—as compared with said Rio Oso Gem peach—by general similarity in size, color, and firmness of flesh, but being more nearly round, with a smooth instead of a rough suture line, a delicate flavor with less acidity, and better eating quality; and additionally characterized by the tree being larger, and more vigorous and productive than said Rio Oso Gem peach tree.

No references cited.